United States Patent [19]
Arnold

[11] Patent Number: 5,578,054
[45] Date of Patent: Nov. 26, 1996

[54] METHOD FOR HAIR TRANSPLANTATION

[76] Inventor: James E. Arnold, 24142 Big Basin Way, Saratoga, Calif. 95070

[21] Appl. No.: 298,823

[22] Filed: Aug. 31, 1994

[51] Int. Cl.$^6$ .................... A61F 2/10; A61B 17/322
[52] U.S. Cl. .................... 606/185; 606/184; 606/187; 606/167
[58] Field of Search ............... 606/185–187, 606/131–133, 167, 184

[56] References Cited

U.S. PATENT DOCUMENTS

| | | | |
|---|---|---|---|
| 3,522,809 | 8/1970 | Cornell | 606/131 |
| 4,122,855 | 10/1978 | Tezel | 606/131 |
| 5,026,385 | 6/1991 | Schutte et al. | |
| 5,060,658 | 10/1991 | Dejter, Jr. et al. | |
| 5,269,801 | 12/1993 | Shiau | |
| 5,439,475 | 8/1995 | Bennett | |

FOREIGN PATENT DOCUMENTS

| | | | |
|---|---|---|---|
| 2666978 | 3/1992 | France | 606/187 |
| 1474175 | 5/1977 | United Kingdom | 606/132 |

OTHER PUBLICATIONS

Charles Monell et al., "The Success or Failure of the Hair Transplant", Arch Otolaryngol, vol. 97, pp. 265–268, Mar. 1973.
Premier Medical Products, "Dermal and Footcare Specialty Products", 3 pages.
Fray Products Corp., "Biopsy Punch".
Brandy, et al., Utilization of No–Kor Needles For Slit–Micrografting, Dermatol Surg Oncol, vol. 20, 1994, pp. 336–339.

Primary Examiner—Robert A. Hafer
Assistant Examiner—Benjamin Koo
Attorney, Agent, or Firm—Townsend & Townsend & Crew LLP

[57] ABSTRACT

The invention provides a device and method for the surgical transplantation of hair. According to the method, an instrument having a shaft and a blade that is attached to the shaft normal to the axis of the shaft is inserted into the skin to a preselected depth as determined by a stop disposed along the shaft to form an incision. The instrument is removed from the skin and a graft of skin having at least one hair is placed in the incision.

24 Claims, 8 Drawing Sheets

METHOD FOR HAIR TRANSPLANTATION

BACKGROUND OF THE INVENTION

The invention provides a device and method for hair transplantation, and in particular to the formation of incisions for receiving small grafts of hair.

For many individuals, hair loss can be undesirable or even traumatic. For such individuals, many hair replacement alternatives have been proposed including wigs, hair pieces, and more recently hair transplants. To some individuals, the hair transplant alternative is particularly desirable because living hair can be used to cover bald areas. As methods for hair transplantation continue to improve, this hair replacement alternative is becoming more widely accepted.

In a typical hair transplantation procedure, grafts of skin containing hair are removed from the individual and are transplanted to other areas. To place the grafts into these areas, a number of incisions are made in the scalp. The incisions are then cleaned and a graft is inserted into each incision. When placing the grafts into the incisions, the surgeon attempts to arrange the grafts so that the resulting transplant resembles a normal hairline. To accomplish such a task, it is desirable in some cases to place only a small number of hairs, i.e. 2 to 6, often referred to as a minigraft (or even a single hair, referred to as a micrograft) into the incisions.

Over the years, a variety of techniques have been employed to transplant minigrafts. In one attempt, the use of a dilator has been proposed. According to this method, an 18 or 20 gauge hypodermic needle is employed to form an incision. A dilator is then placed in the incision to dilate the incision. After removal of the dilator, the minigraft is inserted. Over time, the incision shrinks so that the skin will support the graft. However, until the incision shrinks, the graft is unstable and can be displaced.

In other proposed methods, punches have been employed to punch a small diameter hole in the scalp. The graft is then placed in the cylindrical opening left by the punch. In yet another proposed method, a #11 blade (a Lancet blade) has been employed to form an incision for receiving a minigraft. Since the Lancet blade is angled, this method includes the additional step of translating the blade downward at an angle of 45° after the initial insertion so that the bottom of the incision has a constant depth. Having a constant depth is desirable so that the hair follicles in the graft will all be transplanted at the same depth. In a similar procedure, the use of a No-Kor vented needle (Becton Dickinson and Co, Rutherford, N.J.) has been proposed for creating incisions for receiving 1 to 3 haired minigrafts. Such a method is described in, Dominic A. Brandy and Michael Meshkin, Utilization of No-Kor Needles For Slit-micrografting, J Dermatol Surg Oncol, 20:336–339 (1994).

One problem associated with the above procedures is how to control the depth of the incisions. Usually, this is done visually by the surgeon when inserting the blade or punch. However, such constant visual inspection is both time consuming and tedious to the surgeon. Although the Lancet blade is angled to allow easier visual identification of the depth of the cut, use of such a blade still requires the blade to be angled downward so that the incision has a uniform depth. Such a procedure is both time consuming and inconvenient. One particular problem experienced with the use of punches is that the central lumen of the punch often becomes clogged with tissue. The punch then loses its effectiveness until the tissue is removed.

It would therefore be desirable to provide a device and method that could substantially reduce or eliminate such problems. Such a device and method should allow the depth of the incision to be easily and conveniently controlled and should not require substantial manipulation of the blade to form an incision having a constant depth. In the case of punches, the device and method should additionally allow for the creation of a plurality of incisions without having the punch becoming clogged with tissue.

SUMMARY OF THE INVENTION

The invention provides a method for transplanting hair. According to the method, an instrument is provided having a shaft and a blade that is attached to the shaft so that the blade is normal to the axis of the shaft. The blade is inserted into the skin to a preselected depth that is determined by a stop disposed along the shaft. After the incision has been formed, the instrument is removed from the skin and a graft of skin having at least hair is placed into the incision.

The invention further provides an exemplary method for transplanting hair into a linear incision having a uniform depth. According to the method, an instrument is provided with a shaft, a linear blade that is attached to the shaft normal to the axis of the shaft, and a stop disposed along the shaft. The blade is attached to the shaft to form a sharpened distal edge on the shaft. The blade is inserted into the skin to a preselected depth that is determined by the stop. In this way, a linear incision is formed having a length defined by the length of the blade and a uniform depth along the entire length of the incision. After forming the incision, the instrument is removed from the skin and a graft of skin having at least one hair is placed into the linear incision. Preferably, the preselected depth is less than about 6 mm.

In one particular aspect of the method, the shaft is provided with two substantially parallel sides. This distance between the sides defines a thickness of the shaft. According to the method, the thickness of the shaft is varied to vary the thickness of the incision. Preferably, the thickness is varied in the range from about 0.6 mm to 0.65 mm. In another aspect, the length of the blade is varied to vary the length of the incision. Preferably, the length is varied in the range from about 1.5 mm to 2.7 mm. In yet another aspect, the preselected depth is variable and is varied by moving the stop relative to the blade.

In a further step of the method, a plurality of hairs are placed into the incision. In another aspect, a plurality of incisions are formed in the skin. By keeping the stop at a constant distance between the blade, each incision will have the same depth. Alternatively, the distance between the stop and the blade can be varied to vary the depths of the incisions.

In a preferable aspect, engagement of the stop with the skin prevents further penetration of the blade. This is accomplished by providing the instrument with an elongate handle connected to the shaft. In this way, engagement of the handle with the skin prevents further penetration of the blade.

In an alternative method for transplanting hair, an instrument having a cylindrical shaft and a concentric blade that is attached to the shaft normal to the axis of the shaft is inserted into the skin to a preselected depth as determined by a stop disposed along the shaft to form a circular incision. Preferably, the preselected depth is less than about 6 mm. The blade is attached to the shaft to form a sharpened distal edge on the shaft. Since the blade is normal to the shaft, the resulting incision is provided with a uniform depth. The instrument is then removed from the skin, and tissue from the circular incision is removed from the patient. A graft of skin having at least one hair is then placed into the incision.

In a preferable aspect, the preselected depth is variable and is varied by moving the stop relative to the blade. In yet another aspect, a plurality of hairs are placed into the incision. In another aspect, a plurality of incisions are formed in the skin. If the stop is maintained at a constant distance from the blade, each of the incisions will have substantially the same depth.

In one particular preferable aspect, engagement of the stop with the skin prevents further penetration of the blade. Engagement of the stop with the skin can be accomplished by providing the instrument with an elongate handle connected to the shaft so that engagement of the handle with the skin prevents further penetration of the blade.

In another particular aspect, a central lumen extending entirely through the shaft is provided for receiving tissue removed by the blade. Such a configuration allows for a plurality of incisions to be formed by the same instrument without having tissue accumulating near the blade to hinder the blade from forming additional incisions.

The invention provides a surgical device for forming incisions that are to receive grafts of skin having hair. The surgical device includes a elongate shaft having a proximal end and a distal end. A blade is attached to the distal end of the shaft normal to the axis of the shaft. The blade is attached to the shaft to form a sharpened distal edge on the shaft. A stop is disposed at a preselected distance from the blade for preventing penetration of the blade beyond the preselected distance. Preferably, the stop is disposed at a distance that is less than about 6 mm from the blade.

In a preferable aspect, the stop comprises a handle that is attached to the shaft. In one particular aspect, the stop is adjustable relative to the blade so that the preselected distance can be adjusted. Adjustment of the stop can be accomplished by providing an axially translatable member on the handle so that translation of the member adjusts the distance between the stop and the blade. In one exemplary aspect, the handle can be threaded so that axial translation of the member is accomplished by rotating the member around the handle.

In another preferable aspect, the blade is straight or linear and has a length in the range of about 1.5 mm to 2.7 mm. In another aspect, the shaft is rectangular in cross section and includes at least two parallel sides to define a thickness of the shaft. Preferably, the thickness in the range from about 0.6 mm to 0.65 mm.

In still another aspect, the shaft is cylindrical in geometry and has an outer diameter and an inner diameter forming a central lumen. The blade is concentric in geometry is flush with the shaft to provide a sharpened distal edge on the shaft. In this way, the central lumen can be used to receive accumulated tissue so that the surgical device can be used to form a plurality of incisions without being hindered by the accumulated tissue. Preferably, the shaft has an open proximal end which also serves as an air hole to release air when the blade is inserted into the skin.

DETAILED DESCRIPTION OF THE SPECIFIC EMBODIMENTS

Figure 1:
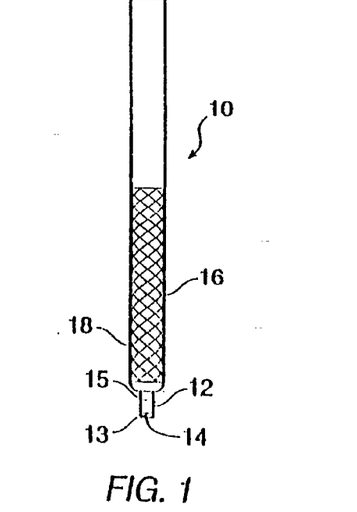
FIG. 1 illustrates a side view of a surgical device having a linear blade according to the present invention.
Figure 2:
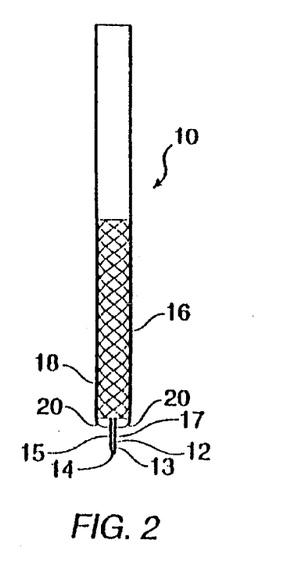
FIG. 2 illustrates the surgical device of FIG. 1 rotated at an angle of 90°.
Figure 3:
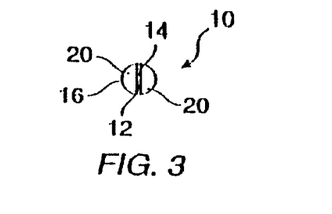
FIG. 3 is a bottom view of the surgical device of FIG. 2.

Referring to FIGS. 1–3, an exemplary embodiment of a surgical device 10 for forming linear incisions in the skin will be described. The device 10 includes a shaft 12 and a blade 14 attached to the shaft 12. The blade 14 is a "chisel" type blade and is straight, i.e. is linear, along its length. The blade 14 is "V shaped" in cross section and is attached at a distal end 13 of the shaft 12 to form a sharpened distal edge on the shaft 12. The shaft 12 is attached to an elongate handle 16 which can conveniently be provided with a gripping surface 18. Preferably, the handle 16 will have a length in the range from about 5 cm to 15 cm, more preferably at about 10 cm.

The shaft 12 and blade 14 are preferably constructed stainless steel. The shaft 12 will preferably be rectangular in cross section (see FIG. 3) and will include at least two substantially parallel walls 15, 17. The distance between the walls 15, 17 defines a thickness of the shaft 12 which will preferably be in the range from about 0.6 mm to 0.65 mm. Such a thickness is useful in forming an incision that is wide enough to receive a graft of hair. As described in more detail hereinafter, a preferable way to vary the thickness of the shaft is simply to replace the shaft. Varying the thickness of the shaft can be desirable when using the shaft to partially dilate the incision to allow easier and faster placement of the grafts.

The length of the blade 14 will preferably be in the range from about 1.5 mm to 2.7 mm. More specifically, a length in the range from about 1.5 mm to 1.6 mm is preferable for forming incisions intended to receive a single hair micrograft. Blades having a length in the range from about 1.8 mm to 1.9 mm are preferable for forming incisions for receiving minigrafts of 2 to 3 hairs, and blade lengths in the range from about 2.5 mm to 2.7 mm are preferred for forming incisions for receiving minigrafts of 3 to 5 hairs. Blades having a length of about 1.5 mm to 1.6 mm can conveniently be formed by removing the distal end of a #61 miniblade, and blades having a length in the range from about 2.5 mm to 2.7 mm can conveniently be formed by removing the distal end of a #62 miniblade.

The handle 16 will preferably be a conventional miniblade handle having a pair of grips 20 for receiving various sized shafts. The shaft 12 is inserted into the grips 20, and the handle is adjusted to clamp the shaft 12 within the grips 20. In this way, the distance between the blade 14 and the handle 16 can be adjusted. Preferably, the distance between the blade 14 and the handle 16 will be less than about 6 mm, and more preferably at about 5 mm. The grips 20 also allow for convenient use of various different sized blades so that a surgeon can tailor the size of the incision to the size of the intended graft.

The diameter of the handle 16 at the grips 20 is greater than the length of the blade 14. With this configuration, the handle 16 acts as a stop when the blade 14 and shaft 12 are inserted into the skin. The blade 14 and shaft 12 will penetrate into the skin until the handle 16 engages the skin. At this point, the handle 16 prevents further penetration of the blade 14 into the skin.

By configuring the surgical device 10 as just described, a surgeon is able to preselect the depth of any incision. Once a depth is selected, a plurality of incisions that each have the same depth can rapidly and conveniently be formed in a patient without visually inspecting the depth of penetration when making each incision. By having the blade 14 being straight and normal to the axis of the shaft 12, each incision can be formed with a uniform depth along its length, i.e. the bottom of the incision is substantially parallel to the scalp at the point of incision. The blade 14 is able to create the incision having the desired depth that is uniform along its length in a single step. In contrast, Lancet blades require at least two steps to create an incision having both a desired depth and one that is uniform along its length as previously described.

Figure 4:
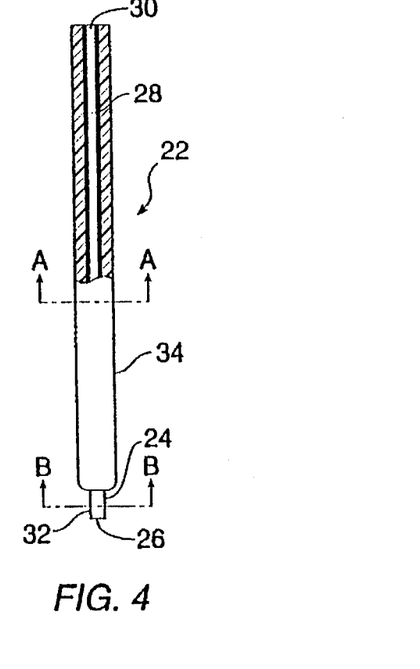
FIG. 4 is a side view of an alternative embodiment of a surgical device having a concentric blade according to the present invention.
Figure 4A:
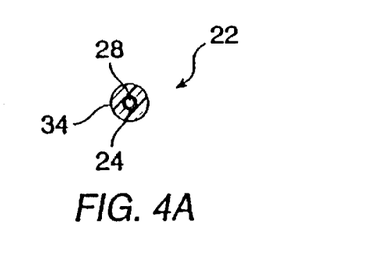
FIG. 4A is a view of the surgical device of FIG. 4 taken along lines A—A.
Figure 4B:
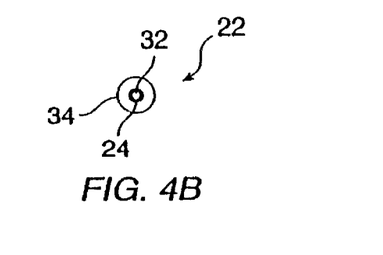
FIG. 4B is a view of the surgical device of FIG. 4 taken along lines B—B.

Referring to FIGS. 4, 4A and 4B, an alternative embodiment of a surgical device 22 will be described. The device 22 includes a cylindrical shaft 24 and a concentric blade 26 attached to the shaft 24. The shaft 24 and blade 26 form what is commonly referred to as a dermal punch. The blade 26 is attached to a distal end 32 of the shaft 24 to form a sharpened distal edge on the shaft. The cylindrical shaft 24 includes a central lumen 28 and is open both at a proximal end 30 and at the distal end 32 where the blade 26 is attached. The shaft 24 is held within a handle 34 which functions as a stop similar to the handle 16 as previously described. Preferably, the blade 26 will be distanced from the handle 34 by a distance that is less than about 6 mm, and preferably at about 5 mm. The blade 26 preferably has an outer diameter in the range from about 1.0 mm to 2.0 mm to form incisions for receiving grafts having 1 to 8 hairs.

The lumen 28 in the shaft 24 is for receiving accumulated tissue from multiple insertions of the blade 26 into the skin. When forming a plurality of incisions, tissue will often build up in the distal end 32 of the shaft 24. By extending the lumen 28 through the entire length of the shaft 24, accumulated tissue can be directed through the lumen 28 upon each additional insertion of the blade 26 to the skin. This prevents the distal end 32 from clogging and increases the effectiveness of the blade 26. The shaft 24 is open at the proximal end 30 so that an air hole can be provided in the shaft 24. This provides for easier travel of the accumulated tissue through the lumen 28. Although the shaft 24 is shown extending entirely through the handle 34, the shaft 24 can terminate anywhere within the handle 24. In such a case, the lumen 28 can be extended through the handle 34 so that an air hole will still be provided. For convenience, the handle 34 can be constructed of plastic or other disposable material so that the device can be discarded after use.

Figure 5:
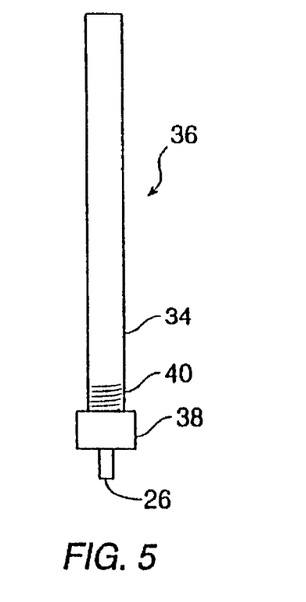
FIG. 5 is a side view of a surgical device having a variable stopping mechanism according to the present invention.

Referring to FIG. 5, an alternative embodiment of a surgical device 36 is shown. The surgical device 36 is essentially identical to the surgical device 22 of FIG. 4 except for the stopping mechanism. For convenience of discussion, the same reference numerals shown in FIG. 4 will be used to describe FIG. 5. The surgical device 36 includes an adjustable stopping mechanism that includes a rotating collar 38 that can be rotated about a plurality threads 40 provided on the handle 34. Rotation of the collar 38 translates the collar 38 axially along the handle 34 and varies the distance between the collar 38 and the blade 26. In this way, the depth of the incision can easily and conveniently be varied by simply rotating the collar 38. The collar 38 engages the skin and prevents further penetration of the blade 26. Although not shown, a variety of different mechanisms can be employed to vary the depth of the incision including adjustable clamps, slidable collars, and the like.

An adjustable collar similar to collar 38 can also be provided on the shaft 12 of the surgical device 10. Such a collar allows the depth of blade penetration to be varied as previously described.

The surgical device 36 is particularly advantageous when forming incisions over a variety of different areas on the scalp. Since the thickness of the scalp varies depending on location, the depth of blade penetration can conveniently be adjusted depending on where the incision is to be made.

Figure 6:
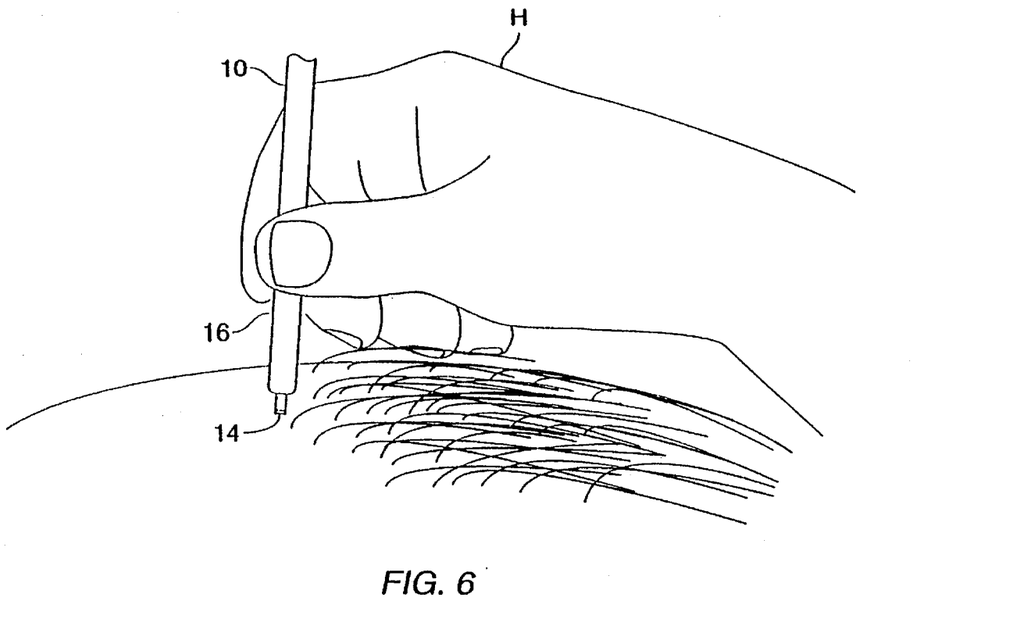
FIGS. 6–9 illustrate an exemplary method for transplanting a graft of skin having hair using a linear incision according to the present invention.
Figure 7:
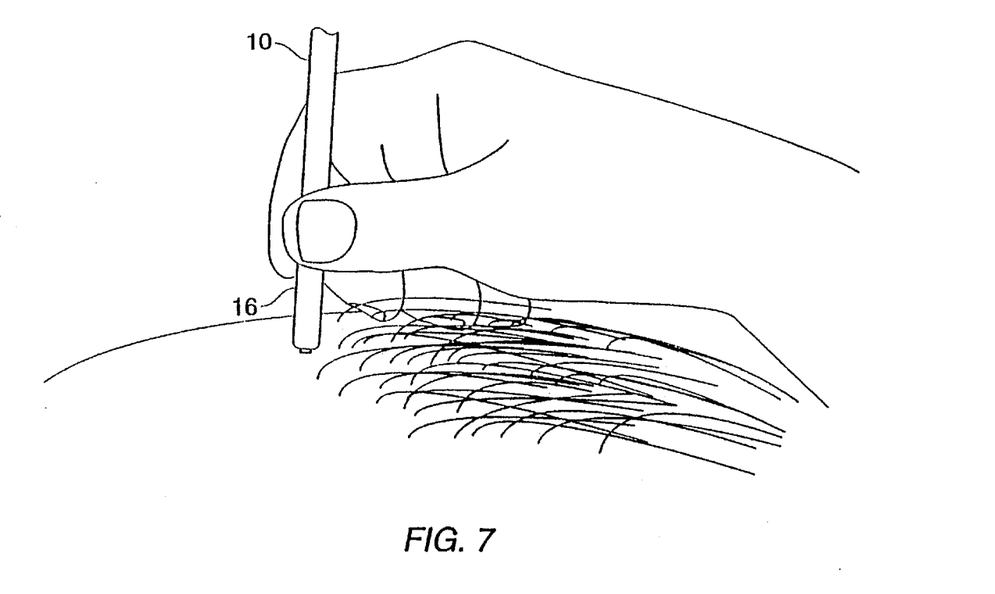
Figure 8:
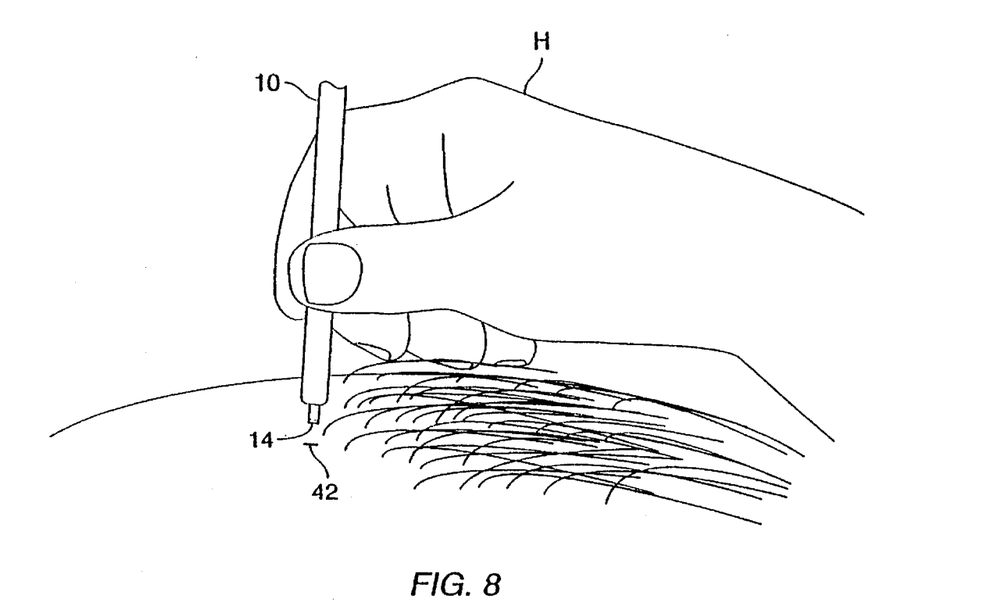
Figure 9:
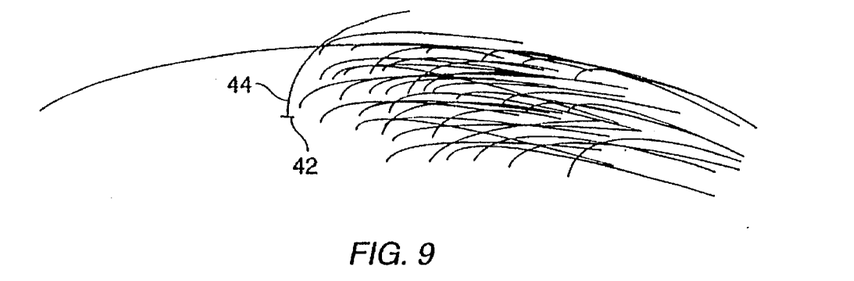

Referring now to FIGS. 6–9, an exemplary method for hair transplantation using the surgical device 10 will be described. As shown in FIG. 6, a surgeon's hand H grasps the device 10 along the handle 16 and positions the blade 14 to a desired location over the patient's scalp. As shown in FIG. 7, the blade 14 is depressed into the patient's scalp by pressing on the handle 16. When pressing the blade 14 into the skin, the handle 16 will preferably be oriented perpendicularly to the patient's scalp at the point of the incision. This allows the blade 14 (that is normal to the shaft 12 and handle 16) to produce an incision having a uniform depth along its length. Penetration of the blade 14 into the scalp is stopped when the handle 16 engages the skin. At that point, the blade 14 has reached the appropriate depth. The device 10 is then lifted from the scalp to remove the blade 14 leaving an incision 42 as shown in FIG. 8. Since the blade 14 is straight, the resulting incision 42 is linear. Having a linear incision is desirable in that it heals quickly and leaves minimal or no scarring. The incision 42 is then cleaned and a micrograft of hair 44 placed therein (see FIG. 9). Alternatively, depending on the size of the incision 42, a minigraft can be placed therein.

The process of forming the incision 42 can be rapidly repeated along the patient's hairline to form a plurality of incisions that each have substantially the same depth, and with each incision having a uniform depth along the lengths of the incisions. Each of these incisions can then have a graft of skin having hair placed therein as previously described.

Figure 10:
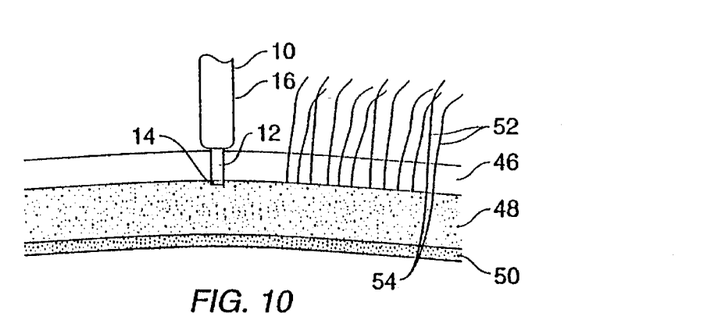
FIGS. 10–12 illustrate in greater detail the method of FIGS. 6–9 showing placement of the blade and the hair graft into the scalp.
Figure 11:
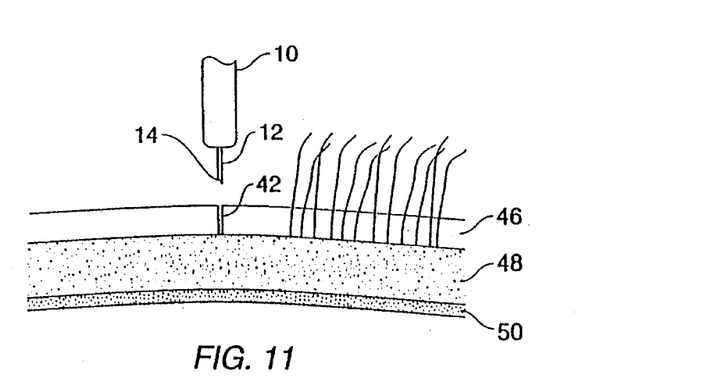
Figure 12:
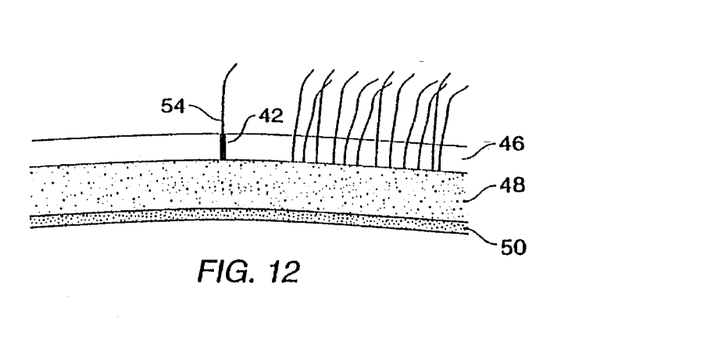

Referring to FIGS. 10–12, formation of the incision 42 will be described in greater detail. As shown in FIG. 10, the patient's scalp includes a dermis layer 46, a fat layer 48 and a galea layer 50. The patient's existing hairs 52 are disposed in the dermis layer 46 with the follicles 54 disposed at the base of the dermis layer 46, with some extending into the fat layer 48. The blade 14 is inserted through the dermis layer 46 until it reaches or slightly penetrates the fat layer 48. At this point, the handle 16 engages the dermis layer 46 and prevents further travel of the blade 14. When the device 10 is lifted from the patient's scalp as shown in FIG. 11, the formation of the incision 42 is complete. The incision has a depth that is uniform along its entire length as previously described. As shown in FIG. 12, a graft of skin having a hair 54 is placed into the incision 42 with the follicle resting near the bottom of the incision 42. As previously described, the depth of the shaft 12 can be adjusted so that the blade 14 will reach an appropriate depth which is preferably near where the dermis layer 46 and the fat layer 48 meet.

Figure 13:
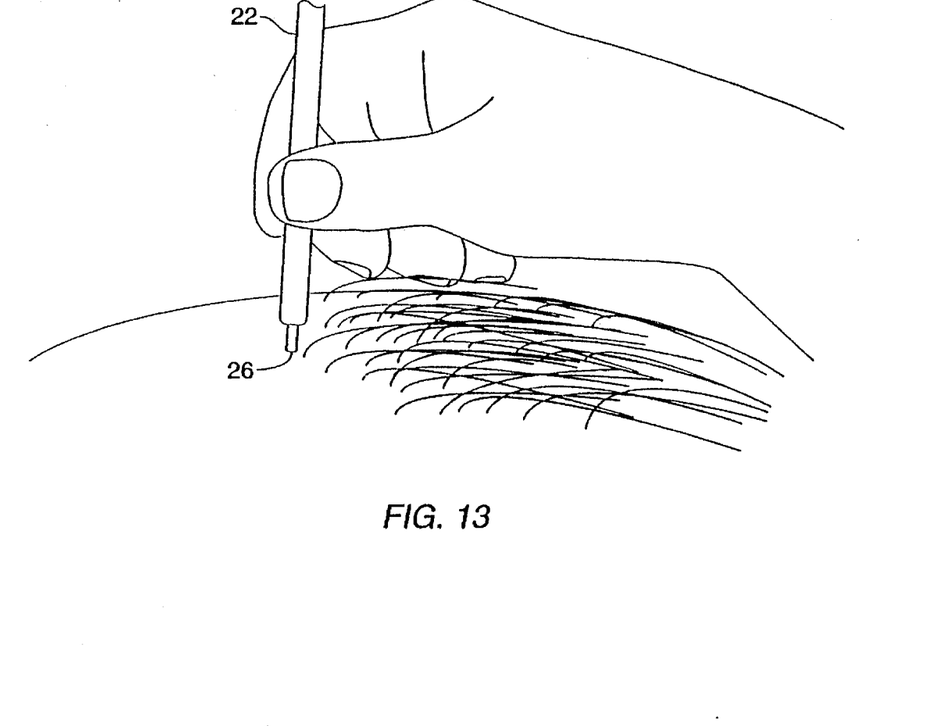
FIGS. 13–17 illustrate an alternative method for transplanting a graft of hair using a surgical device having a concentric blade.
Figure 14:
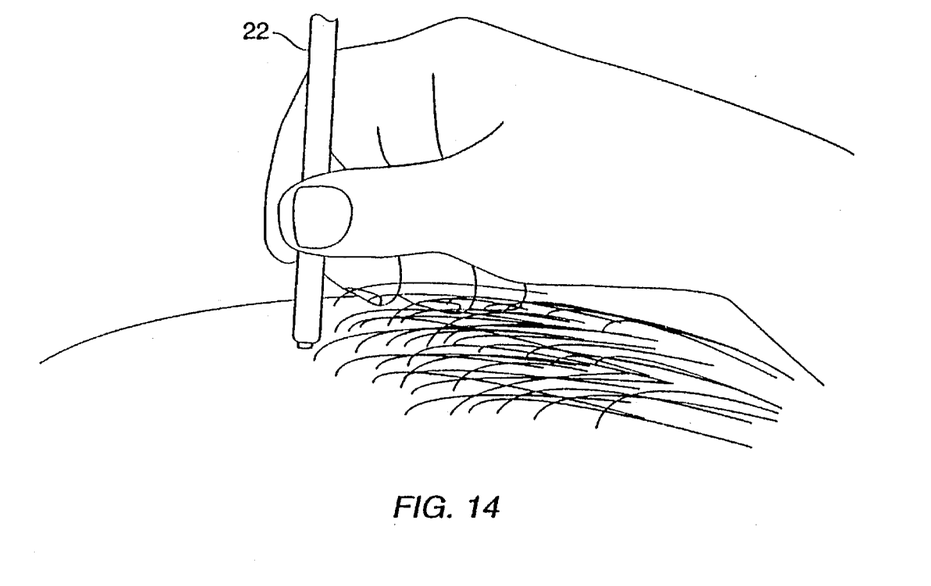
Figure 15:
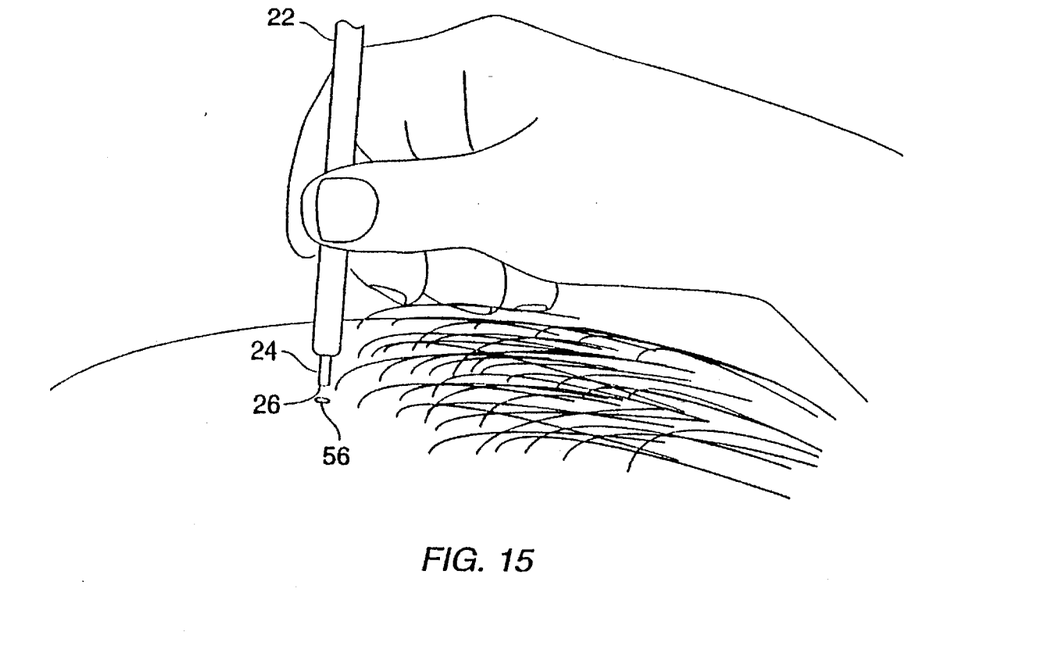
Figure 16:
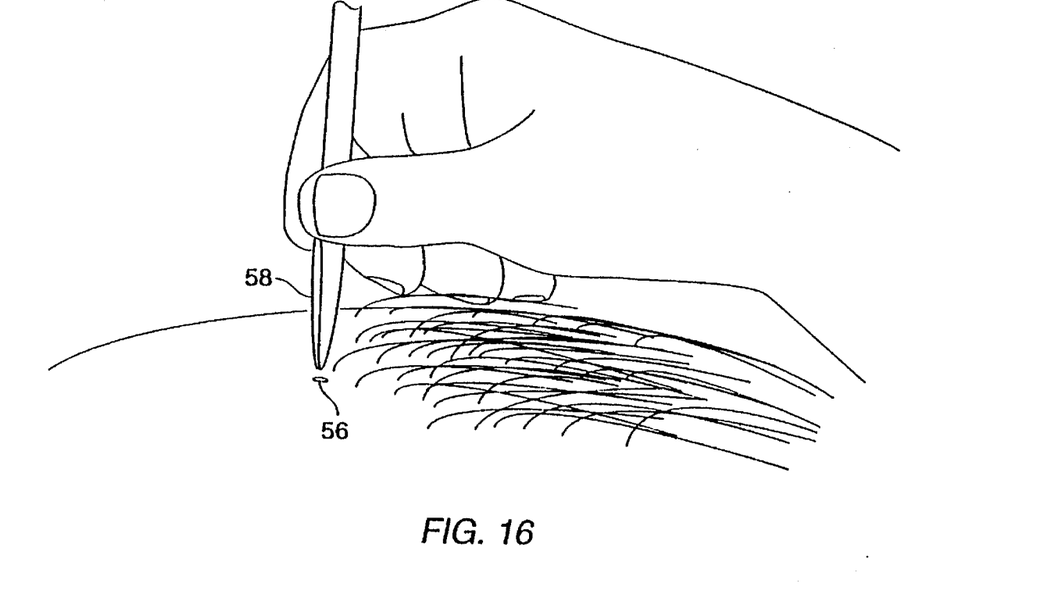
Figure 17:
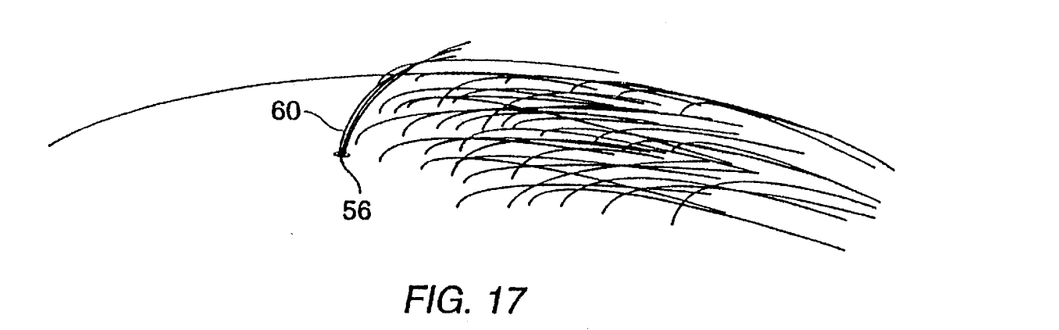

Referring to FIGS. 13–17, a method for transplanting hair using the surgical device 22 will be described. Initially, as shown in FIG. 13, the device 22 is positioned over a patient's scalp with the blade 26 near the patient's hairline. As shown in FIG. 14, the device 22 is depressed to force the blade 26 into the scalp. The device 22 is then lifted from the patient's scalp as shown in FIG. 15. In this way, a circular incision 56 is formed. Sometimes, tissue within the incision 56 will be removed by the shaft 24 when lifting the device 22 from the scalp. If not, a pair of tweezers 58 or other grasping device can be employed to remove the remaining tissue from the scalp as shown in FIG. 16. When the tissue is removed, a cylindrical hole is formed in the patient's scalp. A hair graft 60 can then be placed in incision 56 as shown in FIG. 17.

Although the foregoing invention has been described in detail by way of illustration and example, for purposes of clarity of understanding, it will be obvious that certain changes and modifications may be practiced within the scope of the appended claims.

What is claimed is:

1. A method for transplanting hair, comprising:

inserting an instrument having a shaft with a proximal end, a sharpened distal end forming a blade thereon, and a longitudinal axis extending between the proximal end and the distal end into the skin to a preselected depth as determined by a stop disposed along the shaft to form an incision, wherein the blade is normal to the longitudinal axis of the shaft, wherein the stop prevents the blade from extending beyond about 5 mm into the scalp, and wherein the distance between the blade and the stop is adjusted before inserting the blade;

removing the instrument from the skin; and placing a graft of skin having at least one hair into the incision.

2. A method for transplanting hair, comprising:

providing an instrument having a shaft with a proximal end, a distal end, a longitudinal axis extending between the proximal end and the distal end, the distal end being sharpened to form a linear blade thereon, the blade having a straight edge that is normal to the longitudinal axis of the shaft;

inserting the instrument into the skin to a preselected depth as determined by a stop disposed along the shaft to form a linear incision of a generally constant depth, wherein the preselected depth is about 5 mm or less, and wherein engagement of the stop with the skin prevents further penetration of the blade;

removing the instrument from the skin; and placing a graft of skin having at least one hair into the linear incision.

3. The method of claim 2, further comprising adjusting the distance between the blade and the shaft before inserting the blade, wherein the adjusted distance corresponds to the thickness of the dermis layer.

4. The method of claim 3, wherein the instrument is inserted into the skin with the shaft being substantially perpendicular to the skin at the point of incision, and wherein the shaft is maintained substantially perpendicular to the skin throughout the inserting and removing steps.

5. The method of claim 3, further comprising varying the thickness of the shaft near the blade to vary the thickness of the incision.

6. The method of claim 5, wherein the thickness is varied in the range from about 0.6 mm to 0.65 mm.

7. The method of claim 3, further comprising varying the length of the blade to vary the length of the incision.

8. The method of claim 7, wherein the length is varied in the range from about 1.5 mm to 2.7 mm.

9. The method of claim 2, wherein the preselected depth is variable and is varied by moving the stop relative to the blade.

10. The method of claim 2, further comprising placing a graft of skin having a plurality of hairs into the incision.

11. The method of claim 2, further comprising forming a plurality of incisions in the skin.

12. The method of claim 2, wherein the instrument further includes an elongate handle connected to the shaft, and wherein engagement of the handle with the skin prevents further penetration of the blade.

13. A method for transplanting hair, comprising:

providing an instrument having a tubular shaft with a proximal end, a distal end, a longitudinal axis extending between the proximal end and the distal end, the distal end being sharpened to form a concentric blade thereon, the concentric blade being normal to the longitudinal axis of the shaft;

inserting the instrument into the skin to a preselected depth as determined by a stop disposed along an outer surface of the shaft to form a circular incision of a generally constant depth, wherein the preselected depth is about 5 mm or less, and wherein the distance between the stop and the blade is adjusted prior to inserting the instrument into the skin;

removing the instrument from the skin;

removing tissue from the circular incision formed by the instrument; and placing a graft of skin having at least one hair into the incision.

14. The method of claim 13, wherein the preselected depth is less than 6 mm.

15. The method of claim 14, wherein the instrument is inserted into the skin with the shaft being substantially perpendicular to the skin at the point of incision.

16. The method of claim 13, wherein the preselected depth is variable and is varied by moving the stop relative to the blade.

17. The method of claim 13, further comprising placing a graft of skin having a plurality of hairs into the incision.

18. The method of claim 13, further comprising forming a plurality of incisions in the skin.

19. The method of claim 13, wherein engagement of the stop with the skin prevents further penetration of the blade.

20. The method of claim 13, wherein the instrument further includes an elongate handle connected to the shaft, and wherein engagement of the handle with the skin prevents further penetration of the blade.

21. The method of claim 13, further comprising providing a central lumen extending through the shaft for receiving tissue removed by the blade.

22. A method for transplanting hair, comprising:

providing an instrument having a shaft with a proximal end, a distal end, a longitudinal axis extending between the proximal end and the distal end, the distal end being sharpened to form a linear blade thereon, the blade being straight and being aligned with the longitudinal axis of the shaft;

inserting the instrument into the skin to a preselected depth as determined by a stop disposed along the shaft to form a linear incision of a generally constant depth, wherein the instrument is inserted into the skin with the shaft being substantially perpendicular to the skin at the point of incision, and wherein engagement of the stop with the skin prevents further penetration of the blade;

removing the instrument from the skin, wherein the shaft is maintained substantially perpendicular to the skin throughout the inserting and removing steps; and placing a graft of skin having at least one hair into the linear incision.

23. A method for transplanting hair, comprising:

providing an instrument having a shaft with a proximal end, a distal end, a longitudinal axis extending between the proximal end and the distal end, the distal end being sharpened to form a linear blade thereon, the blade having a straight edge that is normal to the longitudinal axis of the shaft;

adjusting the distance between the blade and the shaft;

inserting the instrument into the skin to a preselected depth as determined by a stop disposed along the shaft to form a linear incision of a generally constant depth, wherein the preselected depth is about 5 mm or less, wherein the distance between the blade and the shaft is adjusted before inserting the blade, and wherein the adjusted distance corresponds to the thickness of the dermis layer;

removing the instrument from the skin; and placing a graft of skin having at least one hair into the linear incision.

24. A method for transplanting hair, comprising:

providing an instrument having a shaft with a proximal end, a distal end, a longitudinal axis extending between the proximal end and the distal end, the distal end being sharpened to form a linear blade thereon, the blade having a straight edge that is normal to the longitudinal axis of the shaft;

inserting the instrument into the skin to a preselected depth as determined by a stop disposed along the shaft to form a linear incision of a generally constant depth, wherein the preselected depth is about 5 mm or less, and wherein the preselected depth is variable and is varied by moving the stop relative to the blade;

removing the instrument from the skin; and placing a graft of skin having at least one hair into the linear incision.

* * * * *